United States Patent
Ishihara (10) Patent No.: US 8,547,425 B2
(45) Date of Patent: Oct. 1, 2013

(54) FLUORESCENCE OBSERVATION APPARATUS AND FLUORESCENCE OBSERVATION METHOD

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 1033 days.

(21) Appl. No.: 12/524,804

(22) PCT Filed: Jan. 30, 2008

(86) PCT No.: PCT/JP2008/051441
§ 371 (c)(1),
(2), (4) Date: Jul. 28, 2009

(87) PCT Pub. No.: WO2008/093746
PCT Pub. Date: Aug. 7, 2008

(65) Prior Publication Data
US 2010/0103250 A1   Apr. 29, 2010

(30) Foreign Application Priority Data

Jan. 31, 2007  (JP) ................. 2007-021559

(51) Int. Cl.
| | |
|---|---|
| *H04N 7/18* | (2006.01) |
| *A61B 3/10* | (2006.01) |
| *A61B 3/04* | (2006.01) |
| *A61B 1/04* | (2006.01) |
| *A61B 1/00* | (2006.01) |
| *A61B 5/00* | (2006.01) |
| *A61B 5/05* | (2006.01) |
| *A61B 6/00* | (2006.01) |
| *A61B 8/00* | (2006.01) |
| *G06K 9/00* | (2006.01) |

(52) U.S. Cl.
USPC ............... 348/77; 348/61; 348/68; 351/205; 351/206; 382/115; 382/128; 382/131; 382/154; 600/112; 600/160; 600/181; 600/317; 600/322; 600/425; 600/433; 600/443; 600/473; 600/476

(58) Field of Classification Search
None
See application file for complete search history.

(56) References Cited

U.S. PATENT DOCUMENTS 5,272,518 A * 12/1993 Vincent ................ 356/405
(Continued)

FOREIGN PATENT DOCUMENTS

JP           07-155285        6/1995
(Continued)

*Primary Examiner* — Ario Etienne
*Assistant Examiner* — Ho Shiu
(74) *Attorney, Agent, or Firm* — Scully, Scott, Murphy & Presser, P.C.

(57) ABSTRACT

The diagnosability of diseased parts is improved by precisely correcting fluorescence images without being affected by specular reflection and without being affected by thick blood vessels. Provided is a fluorescence observation apparatus that includes a light source unit that radiates, onto an observation target site, illumination light that is in the wavelength band absorbed by a blood vessel, first excitation light that includes the wavelength band of the illumination light and generates autofluorescence by exciting an autofluorescent substance in the blood vessel, and second excitation light that is in a different wavelength band from the first excitation light and generates agent fluorescence by exciting fluorescent dye that selectively stains normal tissue and abnormal tissue; an image-acquisition unit that obtains respective images by capturing reflected light, autofluorescence, and agent-fluorescence, obtained by radiating the illumination light, and the first and the second excitation light onto the same observation target site; and an image processing unit that extracts a blood-vessel image from the obtained reflected-light image, obtains a reference image by applying interpolation to an area in the autofluorescence image corresponding to the extracted blood-vessel image, and corrects the agent-fluorescence image, obtained by the image-acquisition unit, based on the obtained reference image.

6 Claims, 12 Drawing Sheets

(56) References Cited

U.S. PATENT DOCUMENTS

| | | | |
|---|---|---|---|
| 5,437,274 A * | 8/1995 | Khoobehi et al. | 600/317 |
| 5,557,349 A * | 9/1996 | Yoneya et al. | 351/206 |
| 5,813,987 A * | 9/1998 | Modell et al. | 600/473 |
| 6,179,421 B1 * | 1/2001 | Pang | 351/205 |
| 6,247,812 B1 * | 6/2001 | Miehle et al. | 351/206 |
| 6,276,798 B1 * | 8/2001 | Gil et al. | 351/206 |
| 6,351,663 B1 * | 2/2002 | Flower et al. | 600/476 |
| 6,496,309 B1 * | 12/2002 | Bliton et al. | 359/618 |
| 6,840,933 B1 * | 1/2005 | Pang et al. | 606/4 |
| 7,201,765 B2 * | 4/2007 | McDaniel | 607/88 |
| 2003/0036751 A1 * | 2/2003 | Anderson et al. | 606/9 |
| 2003/0191368 A1 * | 10/2003 | Wang et al. | 600/160 |
| 2004/0063089 A1 * | 4/2004 | Imaizumi et al. | 435/4 |
| 2004/0210113 A1 * | 10/2004 | Hasegawa | 600/181 |
| 2004/0265915 A1 * | 12/2004 | Schaefer et al. | 435/7.2 |
| 2005/0105683 A1 * | 5/2005 | Sato | 378/62 |
| 2005/0113680 A1 * | 5/2005 | Ikeda et al. | 600/425 |
| 2005/0234302 A1 * | 10/2005 | MacKinnon et al. | 600/181 |
| 2006/0152581 A1 * | 7/2006 | Fukuyama | 348/68 |
| 2006/0184214 A1 * | 8/2006 | McDaniel | 607/89 |
| 2006/0210147 A1 * | 9/2006 | Sakaguchi | 382/154 |
| 2006/0210256 A1 * | 9/2006 | Fukui et al. | 396/67 |
| 2006/0241499 A1 * | 10/2006 | Irion et al. | 600/476 |
| 2007/0043341 A1 * | 2/2007 | Anderson et al. | 606/12 |
| 2007/0166770 A1 * | 7/2007 | Hsieh et al. | 435/7.2 |
| 2007/0172912 A1 * | 7/2007 | Yamamoto et al. | 435/40.5 |
| 2008/0159604 A1 * | 7/2008 | Wang et al. | 382/128 |
| 2008/0177140 A1 * | 7/2008 | Cline et al. | 600/112 |
| 2008/0247622 A1 * | 10/2008 | Aylward et al. | 382/131 |
| 2009/0012378 A1 * | 1/2009 | Ince | 600/322 |
| 2009/0022379 A1 * | 1/2009 | Tashiro et al. | 382/131 |
| 2009/0048516 A1 * | 2/2009 | Yoshikawa et al. | 600/443 |
| 2009/0123365 A1 * | 5/2009 | Yang et al. | 424/1.11 |
| 2009/0129635 A1 * | 5/2009 | Abe | 382/115 |
| 2009/0153798 A1 * | 6/2009 | Dick et al. | 351/206 |
| 2009/0155182 A1 * | 6/2009 | Mauro et al. | 424/9.6 |
| 2009/0203994 A1 * | 8/2009 | Mangat et al. | 600/433 |
| 2011/0157340 A1 * | 6/2011 | Yamazaki et al. | 348/61 |

FOREIGN PATENT DOCUMENTS

| | | |
|---|---|---|
| JP | 9-294706 | 11/1997 |
| JP | 10-243920 | 9/1998 |
| JP | 2002-336187 | 11/2002 |
| JP | 2004-478 | 1/2004 |
| JP | 2006-175052 | 7/2006 |

* cited by examiner

FLUORESCENCE OBSERVATION APPARATUS AND FLUORESCENCE OBSERVATION METHOD

TECHNICAL FIELD

The present invention relates to a fluorescence observation apparatus and a fluorescence observation method

BACKGROUND ART

There is a conventionally known fluorescence-image generating apparatus that radiates excitation light and light that differs in wavelength from the excitation light onto tissue in a body cavity wall and that obtains a fluorescence image based on fluorescence emitted from the tissue due to the excitation light; additionally, it obtains a normalization image based on re-radiated light emitted from the tissue and generates a normalized fluorescence image by dividing the respective acquired fluorescence images by the normalization image (for example, refer to Patent Document 1).

Patent Document 1: Japanese Unexamined Patent Application, Publication No. 2002-336187

DISCLOSURE OF INVENTION

According to the technology in Patent Document 1, when light of the same wavelength as the light from a light source is used as the re-radiated light, in the presence of specular reflection where the light from the light source, after reflection at an observation target site, directly enters an image-acquisition unit, the brightness at that site in the image becomes extremely high. In addition, when autofluorescence generated by blood vessels in the tissue inside the body cavity is used as the re-radiated light, the intensity of autofluorescence from blood vessels differs depending on their thickness.

The present invention has been conceived in consideration of the above-described situation, and an object thereof is to provide a fluorescence observation apparatus and a fluorescence observation method that improve diagnosability of abnormal tissue by precisely correcting fluorescence images over the entire observation target site without being affected by specular reflection and without being affected by thick blood vessels.

A first aspect of the present invention provides an observation apparatus including a light source unit that radiates, onto an observation target site, illumination light in a wavelength band absorbed by a blood vessel, a first excitation light that includes the wavelength band of the illumination light and that excites an autofluorescent substance in the blood vessel to generate autofluorescence, and a second excitation light that excites fluorescent dye that selectively stains normal tissue and abnormal tissue, generating agent fluorescence, and that has a different wavelength band from the first excitation light; an image-acquisition unit that obtains images by respectively capturing reflected light obtained by radiating the illumination light, and autofluorescence and agent-fluorescence obtained by radiating the first and second excitation light onto the observation target site; and an image processing unit that extracts a blood-vessel image from a reflected-light image obtained by the image-acquisition unit, that obtains a reference image by applying interpolation to the area in an autofluorescence image that corresponds to the extracted blood-vessel image, and that corrects an agent-fluorescence image obtained by the image-acquisition unit based on the obtained reference image.

According to the first aspect of the present invention, when illumination light in a wavelength band that is absorbed by blood vessels is radiated onto an observation target site by operating a light source unit, reflected light from the surface of the observation target site is captured by an image-acquisition unit, thereby obtaining a reflected-light image. Here, a blood vessel refers to at least one of the blood vessel itself and the blood flowing therein. Because the illumination light is absorbed by the blood vessel, the reflected-light image becomes darker in parts that contain the blood vessel, thereby making it possible to extract the shapes of thick blood vessels.

Additionally, radiating the first excitation light onto the observation target site by operating the light source unit excites an autofluorescent substance in the blood vessel, thereby generating autofluorescence. Because the autofluorescent substance in each part of the blood vessel generates autofluorescence substantially uniformly in all directions, an autofluorescence image without parts with extremely high brightness is obtained by operating the image-acquisition unit. Here, because the observation target site includes capillary vessels that extend over substantially the entire surface and localized thick blood vessels, the autofluorescence image is an image that includes autofluorescence of the capillary vessels, whose contrast changes depending on the distance with respect to the observation target site, and autofluorescence of the thick blood vessels, which is uniformly bright.

Furthermore, radiating the second excitation light onto the observation target site by operating the light source unit excites fluorescent dye that accumulates specifically in diseased parts, thereby generating agent fluorescence. Then, an agent-fluorescence image, whose contrast changes depending on the distance from the light source unit, is obtained by operating the image-acquisition unit.

By the operating the image processing unit in this state, a blood-vessel image is extracted from the reflected-light image and interpolation is applied to areas of the autofluorescence image that correspond to the extracted blood-vessel image; thereby a reference image with the brightness distribution due to the capillary vessels over the entire surface is obtained. The reference image obtained in this way is an image without parts having extremely high brightness and is an image from which effects of thick blood vessels are removed, and in which the contrast changes depending on the distance. By correcting an agent-fluorescence image using this reference image, regardless of the distance with respect to the observation target site, a fluorescence image with high brightness in a diseased part can be obtained over the entire observation target site; therefore, the diagnosability of abnormal tissue can be improved.

In the above-described first aspect, the light source unit may include a white light source and a wavelength selection unit having a plurality of filters that selectively transmits light in specific wavelength bands in the white light from the white light source.

By doing so, simple switching of the filters by operating the wavelength selection unit allows for easy acquisition of a reflected-light image, autofluorescence image, and agent-fluorescence image at the same observation target site.

In addition, in any of the above-described fluorescence observation apparatuses, it is desirable that the illumination light and the first excitation light be in the same wavelength band.

By doing so, the filter for the illumination light and the filter for the excitation light can be the same filter, enabling a simple configuration.

In addition, in any of the above-described fluorescence observation apparatuses, the wavelength band of the illumination light may contain 415 nm.

Because light in this wavelength band is efficiently absorbed by blood vessels, areas of the reflected-light image that correspond to the thick blood vessels can be accurately extracted.

Further, in the above configuration, the wavelength band of the illumination light may contain 540 nm.

Because light in this wavelength band is efficiently absorbed by blood vessels at deeper positions, it is possible to easily generate a reference image from which the effects of deeply-positioned blood vessels are removed.

In addition, in the above-described first aspect, the image processing unit may include a blood-vessel image-extraction unit that extracts a blood-vessel image based on brightness information of the reflected-light image obtained by the image-acquisition unit, a reference-image generating unit that generates a reference image by applying interpolation, using the brightness of the surrounding area, to the area corresponding to the blood-vessel image in an autofluorescence image obtained by the image-acquisition unit, and a fluorescence-image correcting unit that performs correction by dividing the brightness of the agent-fluorescence image obtained by the image-acquisition unit by the brightness of the reference image.

The blood-vessel image is extracted from the reflected-light image by the operation of the blood-vessel image-extraction unit; the reference image without the effects of thick blood vessels is generated by the operation of the reference-image generating unit, wherein areas of the autofluorescence image that correspond to the blood-vessel image are interpolated using the brightness of the surrounding areas; the effects of distance are removed by the operation of the fluorescence-image correction unit, wherein the brightness value of the agent-fluorescence image is divided by the brightness value of the reference image; and thereby, a fluorescence image in which the diseased part is precisely highlighted is obtained. Accordingly, the diagnosability of diseased parts can be improved.

A second aspect of the present invention provides a fluorescence observation method including a step of radiating, onto the same observation target site, illumination light in a wavelength band absorbed by a blood vessel, a first excitation light that includes the wavelength band of the illumination light and generates autofluorescence by exciting an autofluorescent substance in the blood vessel, and a second excitation light that generates agent fluorescence by exciting fluorescent dye that accumulates specifically in diseased parts and that is in a different wavelength band from the first excitation light; a step of obtaining a reflected-light image, an autofluorescence image, and an agent-fluorescence image by capturing the obtained reflected light, autofluorescence, and agent fluorescence, respectively; a step of extracting a blood-vessel image in the obtained reflected-light image; a step of obtaining a reference image by applying interpolation to an area in the autofluorescence image corresponding to the extracted blood-vessel image; and a step of correcting the agent-fluorescence image based on the obtained reference image.

According to the present invention, it is possible to improve the diagnosability of abnormal tissue by precisely correcting fluorescence images over the entire observation target site without being affected by specular reflection and without being affected by thick blood vessels.

EXPLANATION OF REFERENCE SIGNS

A, B, C filter
$G_2$, $G_2'$ blood-vessel image
$G_3$, $G_6$ autofluorescence image
$G_4$ reference image
$G_5$, $G_5'$ agent-fluorescence image
S observation target site
T blood vessel
X diseased part
1 fluorescence observation apparatus
2 light source unit
4 image processing unit
6 white light source
8 rotating filter (wavelength selection unit)
15 reflected-light image-acquisition device (image-acquisition unit)
16 fluorescence-image-acquisition device (image-acquisition unit)
19 blood-vessel image-extraction unit
20 reference-image generating unit
21 fluorescence-image correcting unit

Best Mode for Carrying out the Invention

A fluorescence observation apparatus 1 according to an embodiment of the present invention will be described referring to FIGS. 1 to 9.

Figure 1:
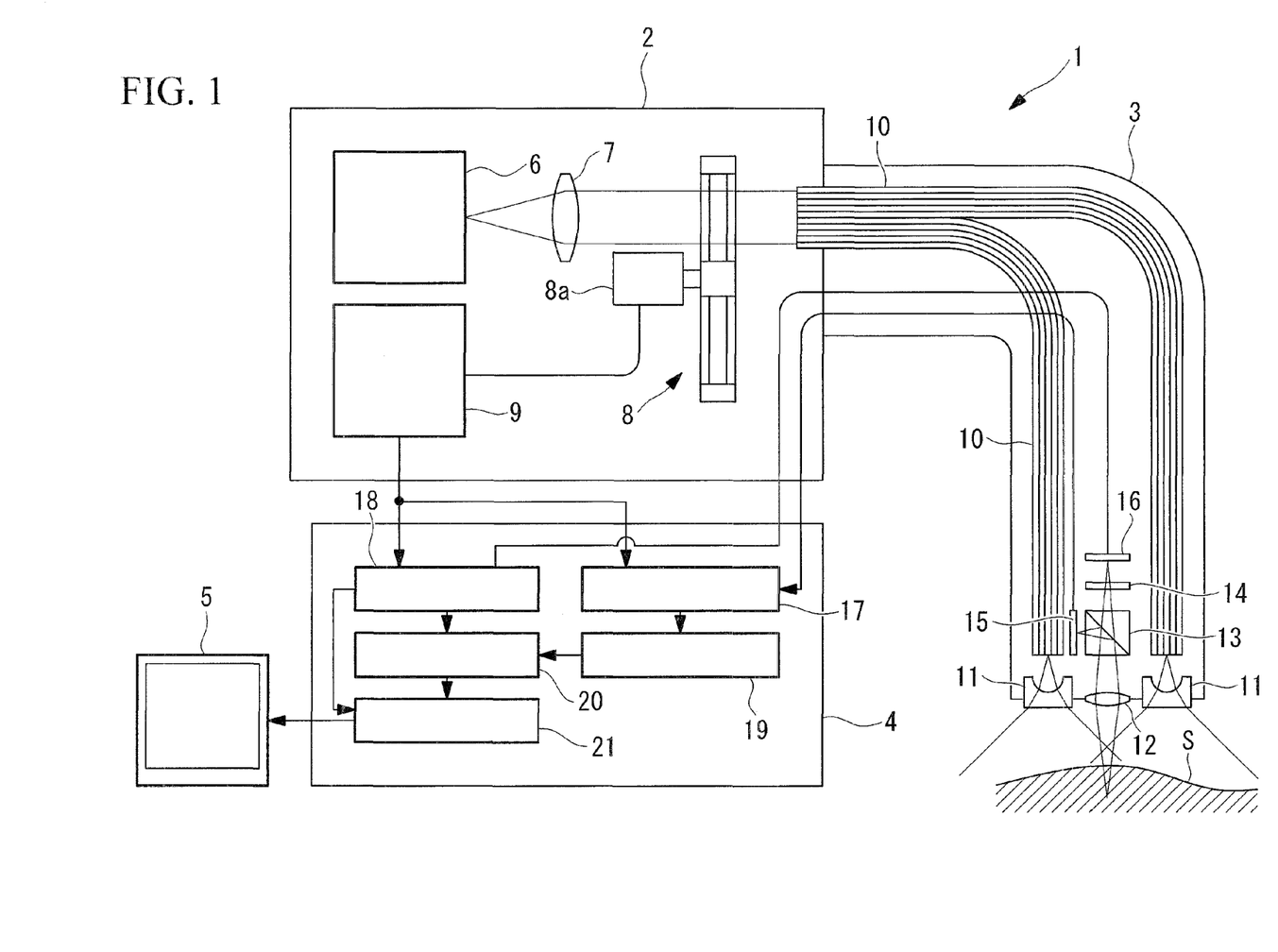
FIG. 1 is a diagram showing a fluorescence observation apparatus according to an embodiment of the present invention.

As shown in FIG. 1, the fluorescence observation apparatus 1 according to this embodiment is provided with a light source unit 2, an insertion unit 3, an image processing unit 4, and a monitor 5.

The light source unit 2 is provided with a white light source 6 that generates white light, a collimating lens 7 that converts the white light from the white light source 6 to a substantially collimated beam, a rotating filter 8 that extracts light in a predetermined wavelength band from the white light, and a filter control unit 9 that controls the rotating filter 8.

Figure 2:
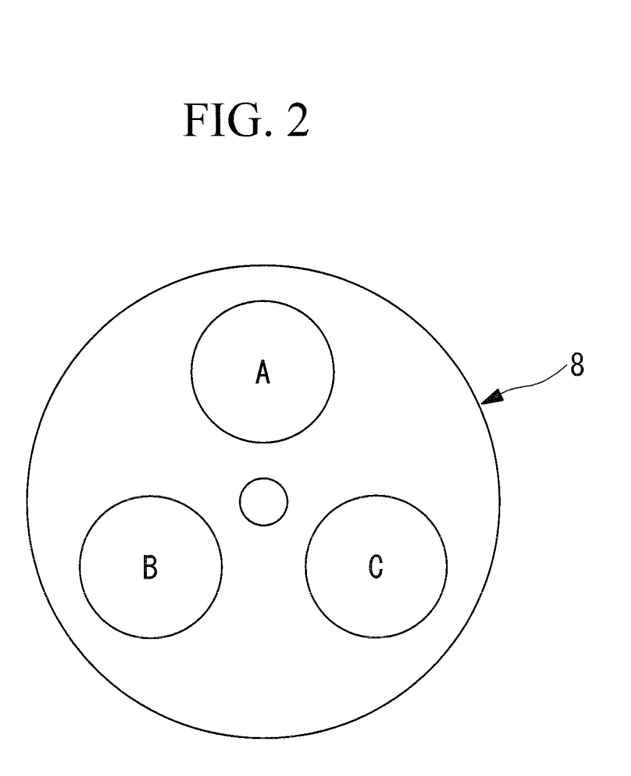
FIG. 2 is a drawing showing an example of a rotating filter included in the fluorescence observation apparatus in FIG. 1.
Figure 3A:
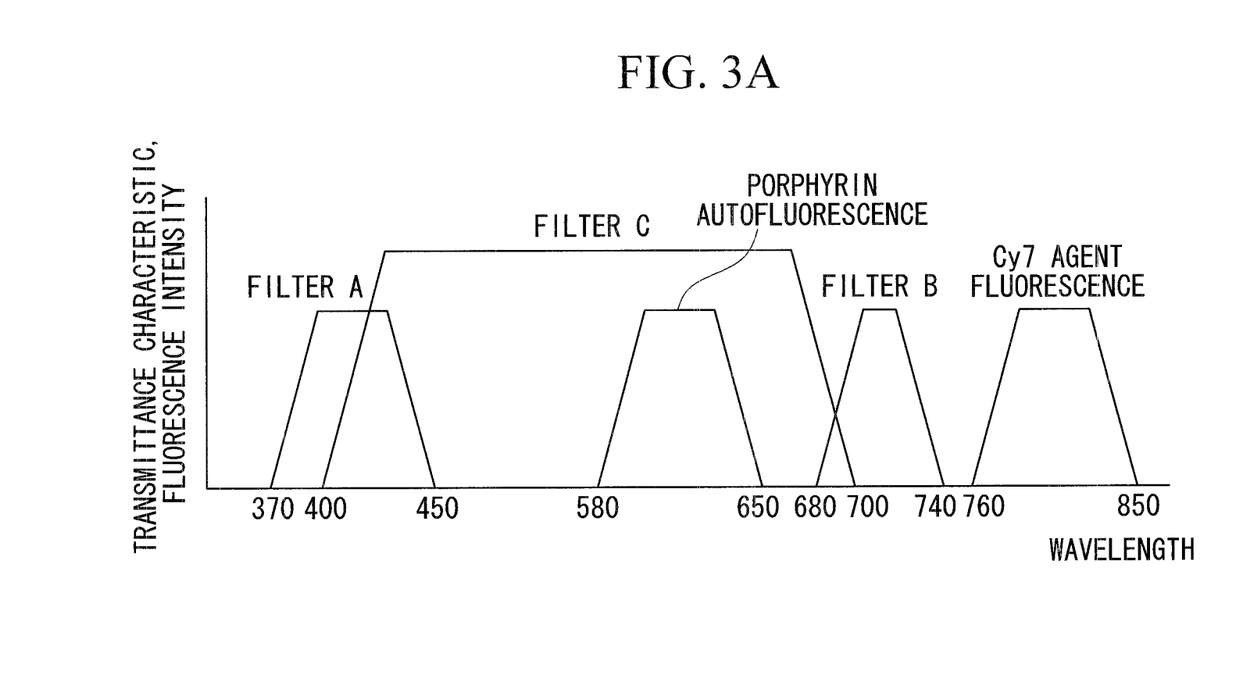
FIG. 3A is a graph showing the transmittance characteristics and the fluorescence-wavelength characteristics of individual filters of the rotating filter in FIG. 2.

As shown in FIG. 2, the rotating filter 8 is provided with three different filters, A, B, and C. These filters A, B, and C, as shown in FIG. 3A, have transmittance characteristics that allows transmission of light in wavelength bands 370-450 nm, 680-740 nm, and 400-700 nm, respectively.

When radiated on an observation target site S, which is living tissue, light in the wavelength band of 370-450 nm extracted by the filter A has a property that it is absorbed by blood vessels or blood flowing in the blood vessels that are located in the living tissue at the observation target site S. In addition, light in this wavelength band has a property that it excites an autofluorescent substance in blood, such as porphyrin, and generates fluorescence in the wavelength band 580-650 nm.

Light in the wavelength band 680-740 nm extracted by the filter B has a property that it excites fluorescence agents, such as Cy 7 (manufactured by Amersham), that accumulate specifically in diseased parts such as tumors, and generates fluorescence in the wavelength band 760-850 nm.

The rotating filter 8 sequentially switches the filters A, B, and C by rotationally driving a motor 8a according to command signals from the filter control unit 9, thereby radiating light in different wavelength bands to the same observation target site S.

In addition, the filter control unit 9 outputs information of the filters A, B, and C, disposed in the optical path, as trigger signals to the image processing unit 4 described later.

The insertion unit 3 is formed thin and bendable so that it can be inserted into a body cavity, for example. The insertion unit 3 is provided with light guide fibers 10 for guiding light emitted from the light source unit 2, a lens 11 that spreads the light guided to the tip by the light guide fibers 10 and radiates it on the observation target site S, an objective lens 12 that collects reflected light or fluorescence returning from the observation target site S, a dichroic mirror 13 that splits the collected reflected light and fluorescence into different optical paths, a barrier filter 14 that blocks the excitation light in the fluorescence that is split off, a reflected-light image-acquisition device 15 that detects the reflected light that is split off, and a fluorescence-image-acquisition device 16 that detects fluorescence that passes through the barrier filter 14.

Figure 3B:
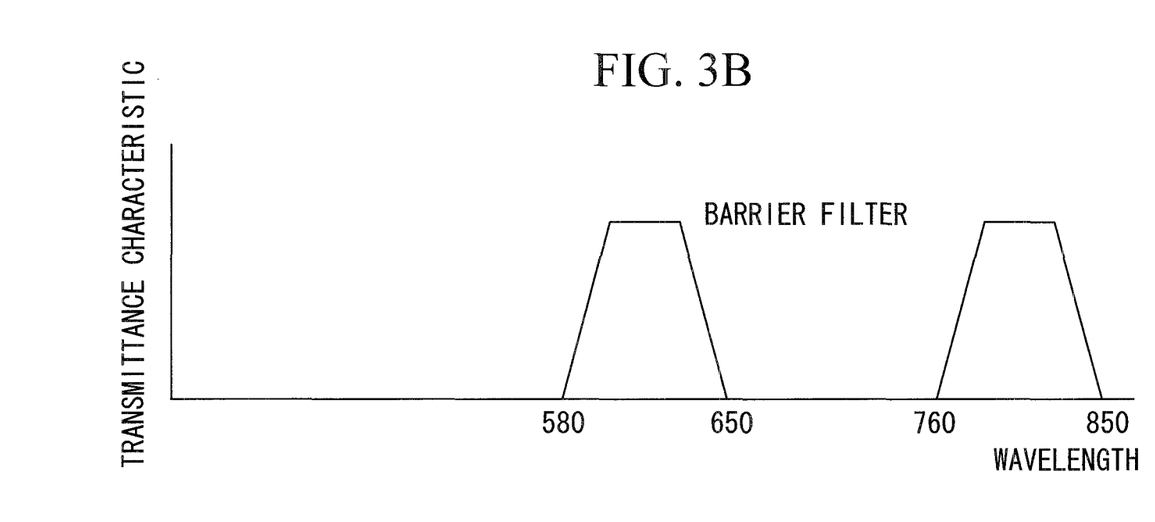
FIG. 3B is a graph showing the transmittance characteristic of a barrier filter.

As shown in FIGS. 3A and 3B, the barrier filter 14 has a transmittance characteristic whereby, of the light split-off from the reflected light by the dichroic mirror 13, it allows passage only of fluorescence in the wavelength band 580-650 nm, corresponding to autofluorescence, and the wavelength band 760-850 nm, corresponding to agent fluorescence, while blocking other light.

Additionally, the reflected-light image-acquisition device 15 and the fluorescence-image-acquisition device 16 are configured individually by solid-state image-acquisition devices such as CCDs.

The image processing unit 4 is provided with a reflected-light image generating unit 17 that generates a reflected-light image based on the reflected-light image information sent from the reflected-light image-acquisition unit 15 and trigger signals sent from the filter control unit 9, a fluorescence-image generating unit 18 that generates an autofluorescence image and an agent-fluorescence image based on the fluorescence-image information sent from the fluorescence-image-acquisition unit 16 and the trigger signals sent from the filter control unit 9, a blood-vessel image-extraction unit 19 that extracts a blood-vessel image from the reflected-light image, a reference-image generating unit 20 that generates a reference image based on the autofluorescence image and the blood-vessel image, and a fluorescence-image correcting unit 21 that corrects the agent-fluorescence image based on the generated reference image.

The reflected-light image generating unit 17 recognizes the period of time for which the filter A is positioned in the optical path using the trigger signals sent from the filter control unit 9 and stores image information sent from the reflected-light image-acquisition unit 15 during this period as a reflected-light image.

The fluorescence-image generating unit 18 recognizes periods of time that the filter A and B are positioned in the optical path, respectively, using the trigger signals sent from the filter control unit 9, stores image information sent from the fluorescence-image-acquisition device 16 during the period that the filter A is positioned in the optical path as an autofluorescence image, and stores image information sent from the fluorescence-image-acquisition device 16 during the period that the filter B is positioned in the optical path as an agent-fluorescence image.

The blood-vessel image-extraction unit 19 performs image processing of a reflected-light image and extracts an image of relatively thick blood vessels. More specifically, the filter A, which is positioned in the optical path when the reflected-light image is generated, extracts light in the wavelength band that is absorbed by blood vessels from the white light.

Figure 4:
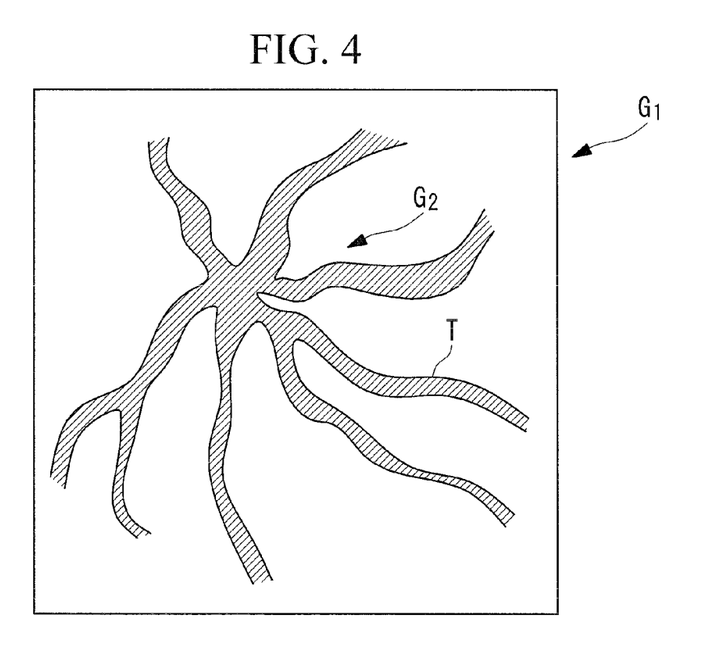
FIG. 4 is a drawing showing an example of a reflected-light image obtained by the fluorescence observation apparatus in FIG. 1.

Accordingly, when light in this wavelength band is radiated, the light is absorbed in areas of the observation target site S that correspond to blood vessels, reducing the light quantity of reflected light therefrom. That is, for a reflected-light image $G_1$, as shown in FIG. 4, an image in which the area corresponding to a blood vessel T is darker than the other areas is obtained. Absorption of light also occurs in other areas because capillary vessels exist uniformly over substantially the entire surface; however, because the volume of blood contained therein is small, absorption to the same degree as with the thick blood vessel does not occur, making them appear brighter than the area corresponding to the thick blood vessel.

Therefore, the area of the thick blood vessel and the other areas can be easily distinguished by applying binarization with a predetermined threshold to the reflected-light image $G_1$, and a blood-vessel image $G_2$ that shows the area of the thick blood vessel can be easily extracted.

The reference-image generating unit 20 generates a reference image $G_4$ based on an autofluorescence image $G_3$ generated by the fluorescence-image generating unit 18 and the blood-vessel image $G_2$ extracted by the blood-vessel image-extraction unit 19.

Because excitation light for generating autofluorescence is light in the same wavelength band as the wavelength band of light absorbed by the blood vessel T, it is absorbed by the blood vessel T and excites an autofluorescent substance in the blood vessel T, such as porphyrin.

Figure 5:
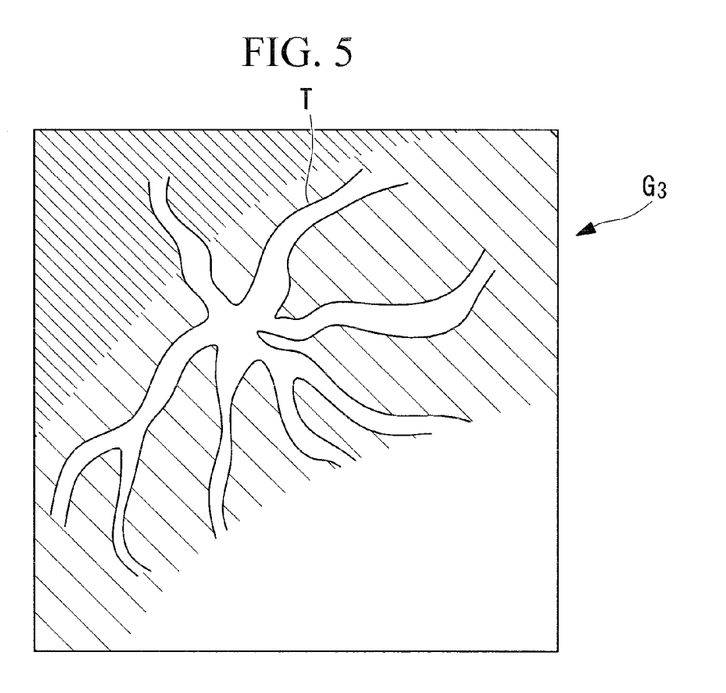
FIG. 5 is a drawing showing an example of an autofluorescence image obtained by the fluorescence observation apparatus in FIG. 1.

Accordingly, in the autofluorescence image $G_3$, the brightness of the area of the thick blood vessel T is the highest, whereas the brightness over substantially the entire surface where capillary vessels exist is lower than that; additionally, it is an image in which, as the distance to the lens 11 that spreads the excitation light increases, the brightness declines in inverse proportion to the square of the distance. For example, as shown in FIG. 5, the autofluorescence image $G_3$ in which brightness increases from the top-left to the bottom-right of the image is obtained. The lens 11 that spreads the excitation light is disposed at the bottom-right. In the example shown in FIG. 5, the area corresponding to the thick blood vessel T has a brightness substantially equal to the brightness of the brightest area at the bottom-right.

In addition, the autofluorescence image $G_3$ is an image without parts with extremely high brightness, because specular reflection of excitation light reflected at the observation target site is prevented from entering the fluorescence-image-acquisition device 16 by the barrier filter 14, and an autofluorescent substance excited in individual parts of the blood vessel T produces autofluorescence substantially uniformly in all directions.

Figure 6:
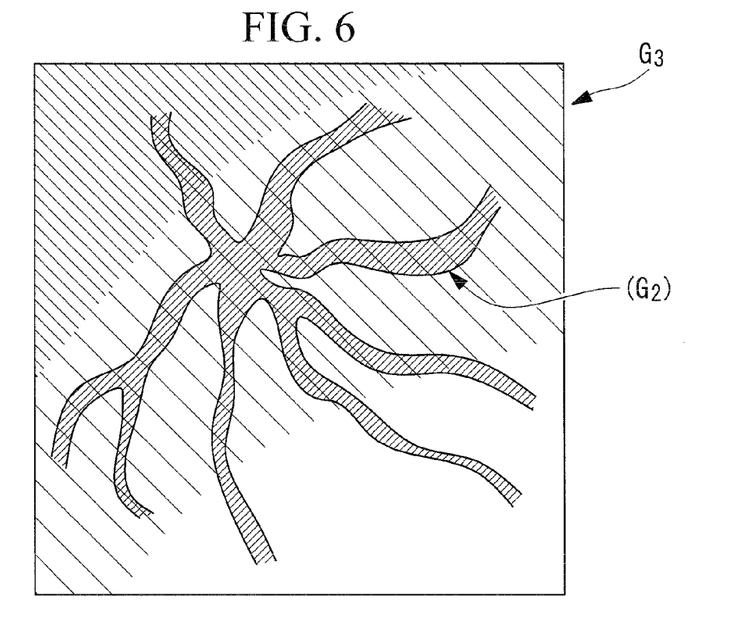
FIG. 6 is a drawing showing an example image in a state in which a blood-vessel image extracted from the reflected-light image obtained with the fluorescence observation apparatus in FIG. 1 is subtracted from the autofluorescence image.

In the reference-image generating unit 20, the blood-vessel image $G_2$ extracted as above is subtracted from such an autofluorescence image $G_3$; thereby, as shown in FIG. 6, the brightness value for the area of the autofluorescence image $G_3$ corresponding to the blood-vessel image $G_2$ can be set to a brightness value that is clearly different from the other areas. In FIG. 6, the site that corresponds to the subtracted blood-vessel image $G_2$ is indicated by the reference sign $(G_2)$.

Figure 7:
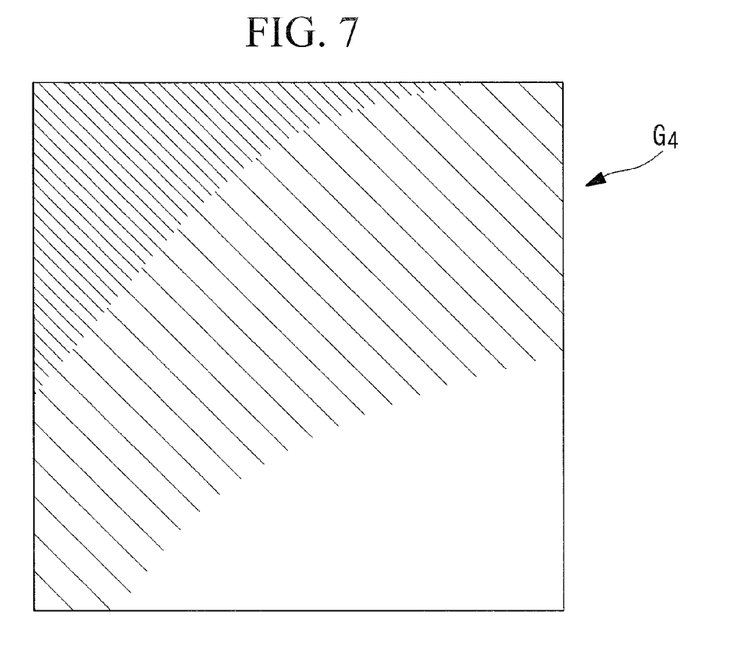
FIG. 7 is a drawing showing an example of a reference image computed by the fluorescence observation apparatus in FIG. 1.

Then, in the reference-image generating unit 20, the area corresponding to the blood-vessel image $G_2$ is eliminated, as shown in FIG. 7, by smoothly interpolating pixels with such a specific brightness value using brightness values of adjacent areas, thereby making it possible to obtain the reference image $G_4$ in which the contrast smoothly changes according to the distance from the lens 11 that spreads the excitation light. For the method of interpolation, any known methods can be used.

Finally, the fluorescence-image correcting unit 21 obtains a corrected agent-fluorescence image $G_5'$ by dividing an agent-fluorescence image $G_5$, generated by the fluorescence-image generating unit 18, by the reference image $G_4$, generated by the reference-image generating unit 20.

Figure 8:
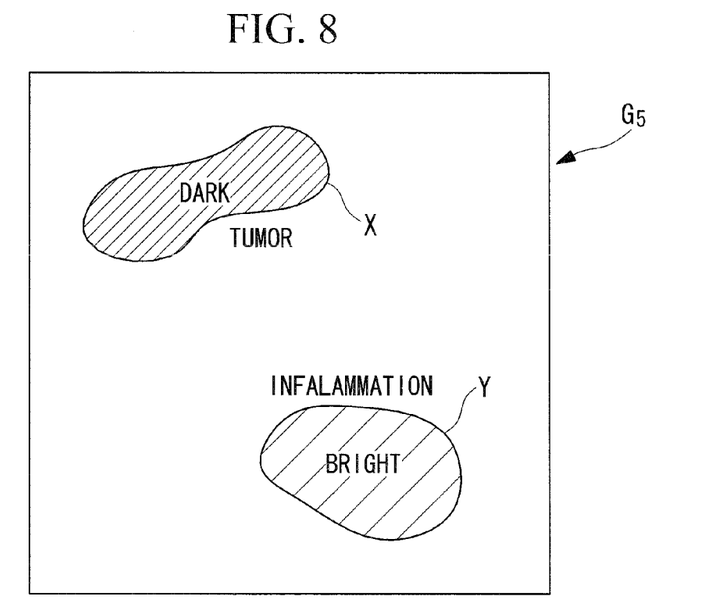
FIG. 8 is a drawing showing an example of an agent-fluorescence image obtained by the fluorescence observation apparatus in FIG. 1.

For example, FIG. 8 shows an example case where the agent fluorescence image $G_5$ with a tumor site X and an inflamed site Y shine with high brightness is obtained and in which the inflamed site Y disposed at a position closer to the lens 11 that spreads the excitation light appears brighter and the tumor site X disposed at a further position appears darker than that.

Figure 9:
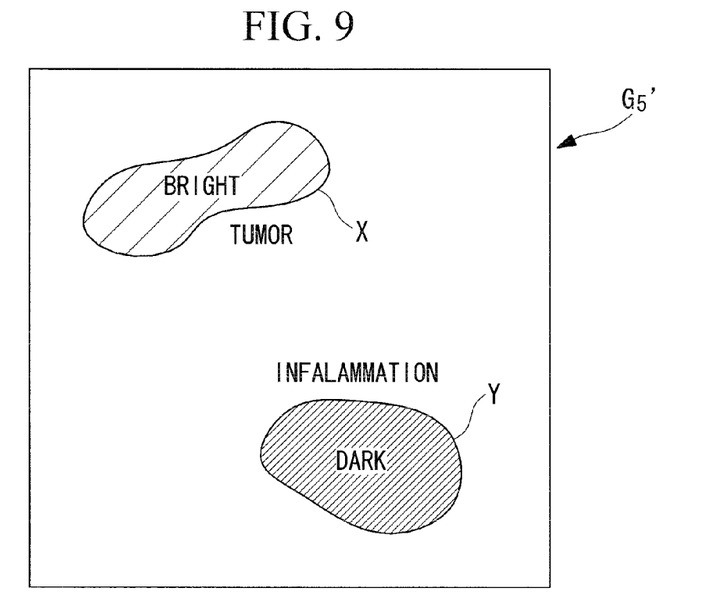
FIG. 9 is a drawing showing an example image produced by correcting the agent-fluorescence image obtained by the fluorescence observation apparatus in FIG. 1 with the reference image.

In this case, if simply this agent fluorescence image $G_5$ alone is observed, it is possible to misdiagnose the brightly appearing inflamed site Y for the tumor site X. Therefore, in the fluorescence-image correcting unit 21, it is possible to normalize the contrast due to the difference in the distance from the lens 11, to generate the corrected agent-fluorescence image $G_5'$ in which the tumor site X that is producing bright fluorescence in reality is made brighter and the inflamed site Y is made darker, as shown in FIG. 9, and to display it on the monitor 5.

A fluorescence observation method using the thus-configured fluorescence observation apparatus 1 according to this embodiment will be described below.

In the fluorescence observation method according to this embodiment, the insertion unit 3 is inserted into the body cavity so that its tip is disposed opposing the observation target site S. In this state, by operating the light source unit 2, light in the wavelength band 370-450 nm, light in the wavelength band 680-740 nm, and white light in the wavelength band 400-700 nm is radiated in a switched manner on the same observation target site S. Here, the white light in the wavelength band 400-700 nm is used in manipulating the insertion unit 3 when confirming the observation target site S with visible light; however, an explanation is omitted herein.

By radiating light in the wavelength band 370-450 nm, the reflected-light image $G_1$ information is obtained by the reflected-light image-acquisition device 15, and autofluorescence image $G_3$ information is obtained by the fluorescence-image-acquisition device 16. In addition, by radiating light in the wavelength band 680-740 nm, agent-fluorescence image $G_5$ information is obtained by the fluorescence-image-acquisition device 16.

In the fluorescence observation method according to this embodiment, the blood-vessel image $G_2$ is extracted from the acquired reflected-light image $G_1$; the blood-vessel image $G_2$ is subtracted from the autofluorescence image $G_3$; the reference image $G_4$ is generated by applying interpolation to the area of the acquired autofluorescence image $G_3$ that corresponds to the blood-vessel image $G_2$; and the agent-fluorescence image $G_5$ is corrected by dividing it by the reference image $G_4$.

Because light in the wavelength band 370-450 nm is absorbed by the blood vessel T, as the reflected-light image $G_1$ information in this case, an image with low brightness in the area of the thick blood vessel T is obtained. Therefore, the area corresponding to the thick blood vessel T can be easily extracted using such reflected-light image $G_1$ information, and the image information in the autofluorescence image $G_3$ that corresponds to the thick blood vessel T can be easily removed.

Because the autofluorescence image $G_3$ is obtained by capturing autofluorescence generated substantially uniformly in all directions from the autofluorescent substance in each part of the blood vessel T, it is an image without parts having extremely high brightness. In addition, because the autofluorescence image $G_3$ is obtained by radiating light in the wavelength band that is absorbed by the blood vessel T, it is obtained by capturing autofluorescence emitted from all parts from the capillary vessels that exist substantially uniformly over the entire surface of living tissue. Because of this, the autofluorescence image $G_3$, from which the information of the thick blood vessel T has been removed, is an image in which brightness varies based on light-distribution characteristics, etc. attributable to, for example, the distance from the lens 11 that spreads light and the position of the lens 11. Therefore, by using this as the reference image $G_4$, there are advantages in that the agent-fluorescence image $G_5'$ normalized by removing such light-distribution characteristics over the entire surface of the observation target site can be easily obtained, and the diseased part can be diagnosed with high precision.

Note that, a case where the rotating filter 8 is provided with three filters A, B, and C is described in this embodiment; however, the filter C for radiating white light is not necessarily required, as described above.

In addition, via the filter A, light in the same wavelength band is used as light radiated on the observation target site S for obtaining the reflected-light image $G_1$ and as light radiated on the observation target site S for obtaining the autofluorescence image $G_3$; however, it is not limited to this.

For example, because the brightness of the autofluorescence image $G_3$ is extremely low compared to the brightness of the reflected-light image $G_1$, in order to obtain a brighter autofluorescence image $G_3$, a separate filter (not illustrated) can be provided to transmit light in a wider wavelength band, including the wavelength band of light radiated to obtain the reflected-light image $G_1$.

Figure 10:
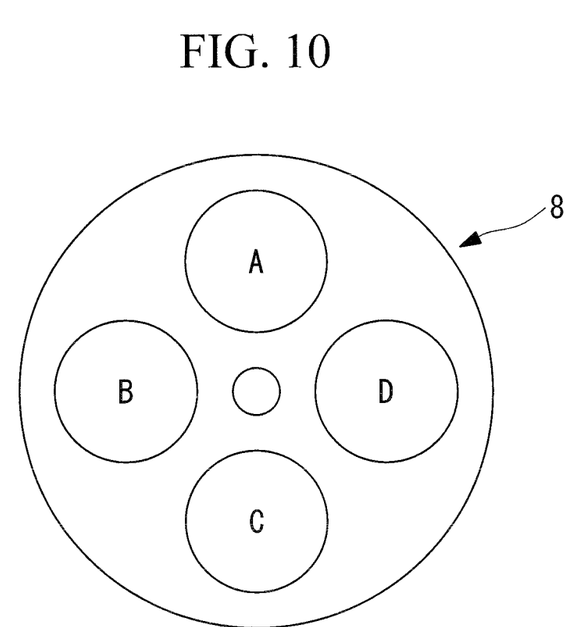
FIG. 10 is a drawing showing a modification of the rotating filter in FIG. 2.
Figure 11A:
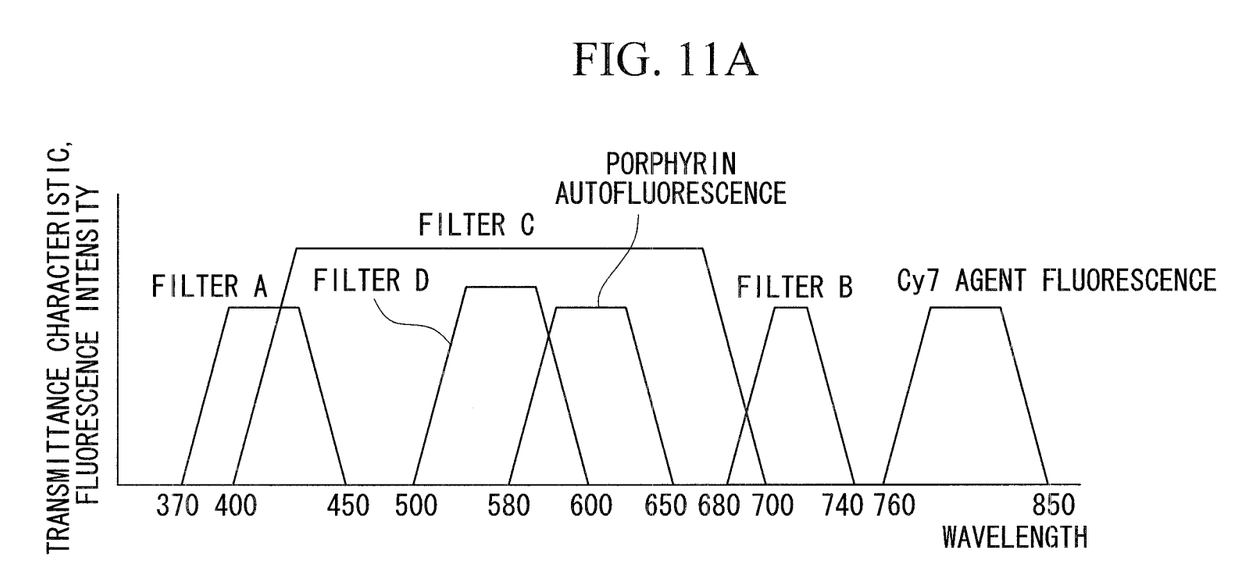
FIG. 11A is a graph showing the transmittance characteristics and the fluorescence-wavelength characteristics of individual filters of the rotating filter in FIG. 10.
Figure 11B:
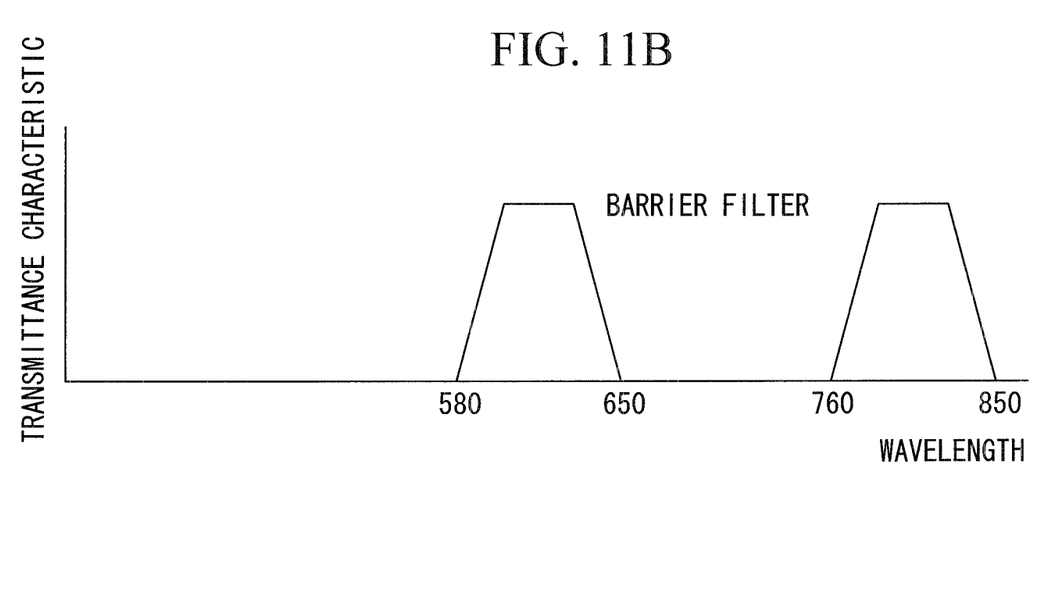
FIG. 11B is a graph showing the transmittance characteristic of a barrier filter included in the fluorescence observation apparatus having the rotating filter in FIG. 10.

Further, in this embodiment, light in the wavelength band 370-450 nm is radiated as the wavelength band absorbed by the blood vessel T; however, in addition thereto, a filter D for radiating light in the wavelength band 500-600 nm may be provided, as shown in FIGS. 10, 11A, and 11B. This light in the wavelength band 500-600 nm is absorbed by the blood vessel T located at a deeper position in living tissue and generates fluorescence; therefore, for example, when there is a thick blood vessel T at a deeper position, as shown in FIG. 12, a blood-vessel image $G_2'$ is included, and an autofluorescence image $G_6$ as shown in FIG. 13 is obtained.

Figure 12:
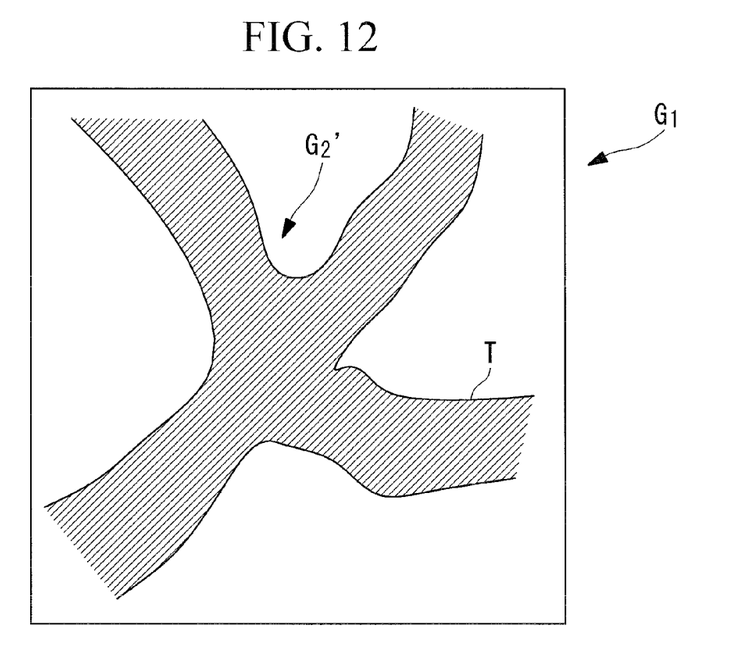
FIG. 12 is a drawing showing an example of a reflected-light image obtained with the fluorescence observation apparatus having the rotating filter in FIG. 10.
Figure 13:
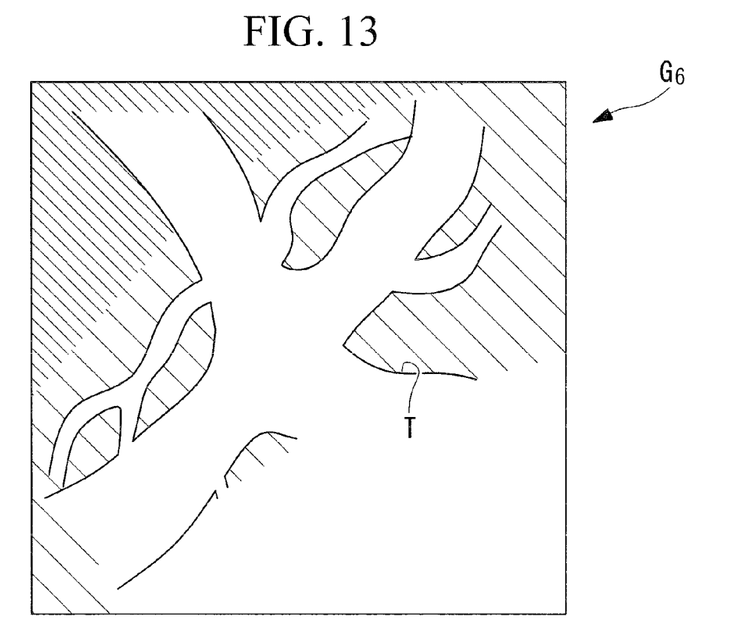
FIG. 13 is a drawing showing an example of an autofluorescence image obtained with the fluorescence observation apparatus in FIG. 12.
Figure 14:
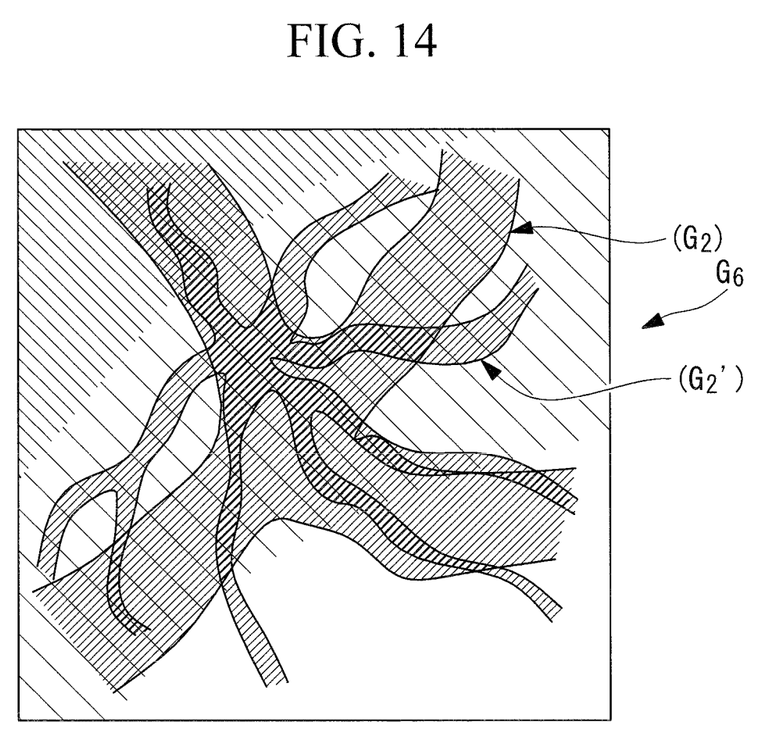
FIG. 14 is a drawing showing an example image in a state in which a blood-vessel image extracted from a reflected-light image obtained with the fluorescence observation apparatus in FIG. 12 is subtracted from the autofluorescence image.

In this case, in addition to the blood-vessel image $G_2$ due to light in the wavelength band 370-450 nm shown in FIG. 4, the blood-vessel image $G_2'$ due to the light in the wavelength band 500-600 shown in FIG. 12 is removed from the autofluorescence image $G_6$, thereby obtaining the image shown in FIG. 14; applying interpolation to this makes it possible to obtain the reference image $G_4$, as shown in FIG. 7, with greater precision. In FIG. 14, sites corresponding to subtracted blood-vessel images $G_2$ and $G_2'$ are indicated by reference signs ($G_2$) and ($G_2'$).

Note that, as for light in the wavelength bands 370-450 nm and 500-600 nm, light in narrower wavelength bands inclusive of the wavelength 415 nm and 540 nm may be adopted.

In addition, the wavelength selection unit is exemplified by the rotating filter 8 including a plurality of filters A, B, and C; however, it is not limited to this, and other variable spectral elements may be adopted.

In addition, the insertion unit 3 may be rigid.

The invention claimed is:

1. A fluorescence observation apparatus comprising:
   a light source unit that radiates, onto an observation target site, illumination light in a wavelength band absorbed by a blood vessel, a first excitation light that includes the wavelength band of the illumination light and that excites an autofluorescent substance in the blood vessel to generate autofluorescence, and a second excitation light that excites fluorescent dye that distinguishably stains normal tissue or abnormal tissue, generating agent fluorescence, and that has a different wavelength band from the first excitation light;
   an image-acquisition unit that obtains images by respectively capturing reflected light obtained by radiating the illumination light, and autofluorescence and agent-fluorescence obtained by radiating the first and second excitation light onto the observation target site; and
   an image processing unit that extracts a blood-vessel image from a reflected-light image obtained by the image-acquisition unit, that obtains a reference image by applying interpolation to the area in an autofluorescence image that corresponds to the extracted blood-vessel image, and that corrects an agent-fluorescence image obtained by the image-acquisition unit based on the obtained reference image, wherein the image processing unit comprises a blood-vessel image-extraction unit that extracts a blood-vessel image based on brightness information of the reflected-light image obtained by the image-acquisition unit, a reference-image generating unit that generates a reference image by applying interpolation, using the brightness of the surrounding area, to the area corresponding to the blood-vessel image in an autofluorescence image obtained by the image-acquisition unit, and a fluorescence-image correcting unit that performs correction by dividing the brightness of the agent-fluorescence image obtained by the image-acquisition unit by the brightness of the reference image.

2. The fluorescence observation apparatus according to claim 1 wherein, the light source unit is provided with a white light source and a wavelength selection unit having a plurality of filters that selectively transmits light in specific wavelength bands in the white light from the white light source.

3. The fluorescence observation apparatus according to claim 1, wherein the illumination light and the first excitation light are in the same wavelength band.

4. The fluorescence observation apparatus according to claim 1, wherein the wavelength band of the illumination light contains 415 nm.

5. The fluorescence observation apparatus according to claim 1, wherein the wavelength band of the illumination light contains 540 nm.

6. A fluorescence observation method comprising:
   a step of radiating, onto the same observation target site, illumination light in a wavelength band absorbed by a blood vessel, a first excitation light that includes the wavelength band of the illumination light and generates autofluorescence by exciting an autofluorescent substance in the blood vessel, and a second excitation light that generates agent fluorescence by exciting fluorescent dye that accumulates specifically in diseased parts and that is in a different wavelength band from the first excitation light;
   a step of obtaining a reflected-light image, an autofluorescence image, and an agent-fluorescence image by capturing the obtained reflected light, autofluorescence, and agent fluorescence, respectively;
   a step of extracting a blood-vessel image in the obtained reflected-light image;
   a step of obtaining a reference image by applying interpolation to an area in the autofluorescence image corresponding to the extracted blood-vessel image;
   a step of correcting the agent-fluorescence image based on the obtained reference image; and
   an image processing step comprising the step of extracting the blood-vessel image based on brightness information of the reflected-light image, wherein the reference image obtaining step generates the reference image by applying interpolation, using the brightness of the surrounding area, to the area corresponding to the blood-vessel image in the autofluorescence image, and wherein the step of correcting the agent-fluorescence image corrects the agent-fluorescence image by dividing the brightness of the agent-fluorescence image by the brightness of the reference image.

* * * * *